United States Patent
Bode

(10) Patent No.: US 10,773,027 B2
(45) Date of Patent: Sep. 15, 2020

(54) INJECTION DEVICE

(71) Applicant: SANOFI-AVENTIS DEUTSCHLAND GMBH, Frankfurt am Main (DE)

(72) Inventor: Andreas Bode, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 64 days.

(21) Appl. No.: 15/558,310

(22) PCT Filed: Mar. 21, 2016

(86) PCT No.: PCT/EP2016/056105
§ 371 (c)(1),
(2) Date: Sep. 14, 2017

(87) PCT Pub. No.: WO2016/150900
PCT Pub. Date: Sep. 29, 2016

(65) Prior Publication Data
US 2018/0243512 A1    Aug. 30, 2018

(30) Foreign Application Priority Data
Mar. 23, 2015   (EP) ..................................... 15160254

(51) Int. Cl.
A61M 5/315    (2006.01)
A61M 5/24     (2006.01)
A61M 5/31     (2006.01)

(52) U.S. Cl.
CPC .......... A61M 5/31573 (2013.01); A61M 5/24 (2013.01); A61M 5/3129 (2013.01);
(Continued)

(58) Field of Classification Search
CPC .. A61M 5/24; A61M 5/31573; A61M 5/3129; A61M 5/31585; A61M 5/31541;
(Continued)

(56) References Cited

U.S. PATENT DOCUMENTS

2003/0100883 A1* 5/2003 Kristensen ............... A61J 1/062
                                                        604/411
2009/0224004 A1   9/2009 Mueller et al.
(Continued)

FOREIGN PATENT DOCUMENTS

CN        1780652        5/2006
CN        101501459      8/2009
(Continued)

OTHER PUBLICATIONS

International Preliminary Report on Patentability in International Application No. PCT/EP2016/056105, dated Sep. 26, 2017, 11 pages.

(Continued)

Primary Examiner — Tiffany Legette
(74) Attorney, Agent, or Firm — Fish & Richardson P.C.

(57) ABSTRACT

The present disclosure relates to an injection device for delivery of a liquid medicament including a housing, a cartridge having a tubular shaped barrel filled with a liquid medicament and sealed in a proximal direction by a piston displaceably arranged in the barrel, and a drive mechanism having a piston rod to advance in a distal direction against a proximally facing surface of the piston of the cartridge. The drive mechanism is configured to advance the piston rod in the distal direction by a distance z1 to dispense a reference volume V1 of the medicament when operably engaged with a reference cartridge having a reference diameter D1, and, the cartridge has a diameter D2 smaller than the reference diameter D1 to dispense a volume V2 of the medicament (Continued)

smaller than the reference volume V1 when the piston rod advances in distal direction by the distance z1.

11 Claims, 4 Drawing Sheets

(52) U.S. Cl.
CPC .... *A61M 5/31551* (2013.01); *A61M 5/31585* (2013.01); *A61M 5/31541* (2013.01); *A61M 5/31556* (2013.01); *A61M 2005/2407* (2013.01); *A61M 2005/2492* (2013.01); *A61M 2005/3126* (2013.01)

(58) Field of Classification Search
CPC ...... A61M 5/31556; A61M 2005/2407; A61M 2005/2492; A61M 2005/3126
See application file for complete search history.

(56) References Cited

U.S. PATENT DOCUMENTS

| | | | |
|---|---|---|---|
| 2010/0036320 A1 | 2/2010 | Cox et al. | |
| 2013/0096510 A1* | 4/2013 | Plumptre | A61M 5/24 604/189 |
| 2013/0274661 A1* | 10/2013 | Teucher | A61M 5/24 604/110 |
| 2013/0288968 A1* | 10/2013 | George | A61K 9/0019 514/10.4 |
| 2014/0249482 A1* | 9/2014 | Wieselblad | A61M 5/31551 604/211 |
| 2014/0257197 A1* | 9/2014 | Madsen | A61M 5/31585 604/228 |

FOREIGN PATENT DOCUMENTS

| | | |
|---|---|---|
| CN | 104010677 | 8/2014 |
| CN | 104427972 | 3/2015 |
| JP | 2009-540986 | 11/2009 |
| JP | 2011-530337 | 12/2011 |
| WO | WO 03/17914 | 3/2003 |
| WO | WO 2004/078240 | 9/2004 |
| WO | WO 2004/078241 | 9/2004 |
| WO | WO 2007/107431 | 9/2007 |
| WO | WO 2008/003560 | 1/2008 |
| WO | WO 2010/017285 | 2/2010 |
| WO | WO 2011/131776 | 10/2011 |
| WO | WO 2014/005728 | 1/2014 |

OTHER PUBLICATIONS

International Search Report and Written Opinion in International Application No. PCT/EP2016/056105, dated Sep. 19, 2016, 19 pages.

* cited by examiner

INJECTION DEVICE

CROSS REFERENCE TO RELATED APPLICATIONS

The present application is the national stage entry of International Patent Application No. PCT/EP2016/056105, filed on Mar. 21, 2016, and claims priority to Application No. EP 15160254.7, filed in on Mar. 23, 2015, the disclosures of which are expressly incorporated herein in entirety by reference thereto.

TECHNICAL FIELD

The present disclosure relates in one aspect to an injection device, such like a pen-type injector operable for setting and dispensing of a dose of a medicament. In particular, the disclosure relates to a cartridge filled with a liquid medicament, which cartridge is of reduced diameter compared to standard sized cartridges conventionally used with pen-type injection devices. In another aspect the disclosure relates to a method of improving the dosing accuracy of an injection device.

BACKGROUND

Injection devices for setting and dispensing a single or multiple doses of a liquid medicament are as such well-known in the art. Generally, such devices have substantially a similar purpose as that of an ordinary syringe.

Injection devices, in particular pen-type injectors have to meet a number of user-specific requirements. For instance, with patient's suffering chronic diseases, such like diabetes, the patient may be physically infirm and may also have impaired vision. Suitable injection devices especially intended for home medication therefore need to be robust in construction and should be easy to use. Furthermore, manipulation and general handling of the device and its components should be intelligible and easy understandable. Moreover, a dose setting as well as a dose dispensing procedure must be easy to operate and has to be unambiguous.

Typically, such devices comprise a housing including a particular cartridge holder, adapted to receive a cartridge at least partially filled with the medicament to be dispensed. Such devices further comprise a drive mechanism, usually having a displaceable piston rod which is adapted to operably engage with a piston of the cartridge. By means of the drive mechanism and its piston rod, the piston of the cartridge is displaceable in a distal direction or dispensing direction and may therefore expel a predefined amount of the medicament via a piercing assembly, which is to be releasably coupled with a distal end section of the housing of the injection device.

The medicament to be dispensed by the injection device is provided and contained in a multi-dose cartridge. Such cartridges typically comprise a vitreous barrel sealed in distal direction by means of a pierceable seal and being further sealed in proximal direction by the piston. With reusable injection devices an empty cartridge is replaceable by a new one. In contrast to that, injection devices of disposable type are to be discarded when the medicament in the cartridge has been dispensed or used-up.

Existing and commercially distributed pen-injectors may be equipped with cartridges providing a predefined volume for a liquid medicament, e.g. 3 ml. The injection devices are typically configured to provide user-operated variable setting of a dose and subsequent dispensing or delivery thereof. Typically, a dose can be selected and dispensed in discreet steps of e.g. one or several International Units (IU). Most injection devices on the market are configured and designed for use of grown up patients.

In the field of pediatric treatment it is desirable to reduce the dose of medicaments and to administer non-integer amounts of IU to a patient. This requires smaller dose increments to be selectable. It is therefore desirable to set and to dispense doses having a size of less than one IU, e.g. of half units. Hence, it is desirable to provide dose setting with increments of half units or less in order to increase dosing accuracy and to allow for a finely segmented, precise setting and dispensing of doses of a particularly small size.

In order to meet these requirements existing injection devices require modifications.

SUMMARY

Certain aspects of the present disclosure provide a rather simple approach to enable setting and dispensing of doses of reduced size, in particular to provide setting and dispensing of half units or other non-integer units of a liquid medicament by making use of an existing drive mechanism of an injection device. The present disclosure relates to modifications to an existing injection device, which modifications are simple and cost efficient to realize.

In a first aspect an injection device for delivery of a liquid medicament is provided. The injection device, typically of pen-injector type comprises a housing to accommodate a cartridge and a drive mechanism. The cartridge also belonging to the injection device comprises a tubular-shaped barrel filled with a liquid medicament. The cartridge is sealed in a proximal direction by a piston that is displaceably arranged inside the barrel. At a distal end the cartridge is typically provided with a pierceable seal acting and serving as a septum. For delivery of the liquid medicament, in particular for injecting of a dose of the liquid medicament into biological tissue the distal seal of the cartridge is to be pierced and penetrated by a double-tipped injection needle in such a way, that a proximally directed tapered or tipped end of the injection needle is located in the interior volume of the cartridge. Then, by exerting a distally directed pressure onto the piston the piston is advanced in distal direction by a predetermined distance thereby expelling a predefined amount of the medicament through the injection needle.

The injection device further comprises a drive mechanism having a piston rod to advance in a distal direction. The piston rod is configured to abut against a proximally facing surface of the piston of the cartridge. The drive mechanism is typically configured to provide setting and dispensing of doses of variable size. The drive mechanism typically comprises a dose setting member and a dose dispensing member that provide individual and variable setting and dispensing of a dose by the end user or patient. However, the injection device is not limited to drive mechanisms providing variable and user settable dose dispensing but the disclosure may also relate to so called fixed dose injection devices that provide repeated delivery of a dose of the medicament of constant size.

The drive mechanism of the injection device is configured to advance the piston rod in distal direction by a distance $z_1$ in order to dispense a reference volume $V_1$ of the medicament when operably engaged with a reference cartridge having a reference diameter $D_1$.

Hence, the drive mechanism may be configured for standard sized cartridges, e.g. having an effective filling volume of about 3 ml. Dose setting and dose dispensing as indicated to the user, e.g. by a dose indicating member or dose indicating sleeve of the drive mechanism, is configured and adapted in accordance with the dispensing rate of the medicament arising when the piston is displaced in axial direction by a predefined distance. Depending on the geometry, in particular depending on the size of the cross-section of the tubular-shaped barrel of the cartridge a displacement z1 of the piston corresponds to the ejection of a volume V1 that is given by a multiplication of the axial displacement z1 with the transverse cross-sectional area of the piston of the cartridge.

In the present context the axial direction points along the longitudinal or main cylinder axis of the tubular-shaped barrel whereas the transverse direction points perpendicular to the longitudinal direction. Furthermore, the distal direction denotes the direction pointing towards an injection site of a patient whereas the proximal direction is directed towards the opposite end of the device. An injection needle is typically arranged at a distal end of the device whereas dose setting and/or dose dispensing members of the drive mechanism are typically located at the opposite proximal end of the injection device.

The cartridge actually arranged inside the housing of the injection device has a diameter D2 that is smaller than the reference diameter D1. In this way a volume V2 of the medicament being smaller than the reference volume V1 can be dispensed when the piston rod advances in distal direction by the distance z1. Hence, one aspect of the disclosure is particularly dedicated to replace a standard sized cartridge by a cartridge with a reduced diameter or reduced cross-section. In this way, the ejected volume per axial displacement of the piston can be effectively reduced.

Consequently, a diameter reduced cartridge can be used with a totally unaltered drive mechanism in order to dispense particularly small sized doses of the medicament. In this way, dosing accuracy can be enhanced rather easily. When replacing a standard sized cartridge by a diameter reduced cartridge the step size of discrete dose sizes to be set and dispensed by the device can be effectively reduced. Hence, with a drive mechanism originally intended to set and to dispense dose sizes of integer numbers of international units (IU) can be used straight forward to set and to dispense doses of the medicament with sizes of non-integer IU, e.g. of half-units or other fractions of one unit. For instance it is possible to set and to dispense doses of e.g. 1.5 IU, 3.8 IU, 7.5 IU, and so on.

The diameter D2 as well as the reference diameter D1 refer to inner diameters of the tubular-shaped barrel of respective cartridges. With a tubular-shaped barrel with a circular transverse cross-section the volume V1 is related to the distance z1 and to the diameter D1 by the following formula:

$$V1 = \left(\frac{D1}{2}\right)^2 \pi * z1.$$

The same relationship is valid for the diameter reduced cartridge with an inner diameter of D2 smaller than D1.

In order to provide a diameter reduced cartridge it would be sufficient to increase the sidewall thickness of the cartridge while keeping the outer diameter substantially constant. Then, the cartridge according to the present disclosure with a reduced inner diameter could be directly fitted into the housing of the injection device almost without any further modifications to be made to the drive mechanism or to a cartridge holder of the housing of the injection device. It may be only necessary to modify the size of a pressure piece at the distal end of the piston rod so as to match with the reduced diameter or transverse cross-section of the piston, which is equally reduced in diameter.

In other embodiments the diameter reduction of the cartridge also implies a respective geometric modification of a cartridge holder, typically forming a distal end of the housing of the injection device and being particularly configured to accommodate and to house the cartridge therein. In embodiments, wherein also the outer diameter of the cartridge is smaller than the outer diameter of the reference cartridge it is only required that an inner diameter or an inside facing geometry of a size reduced cartridge holder matches with the size reduced outer circumference of the cartridge. The outside facing appearance and geometry of such a cartridge holder can remain unchanged compared to a standard cartridge holder configured to accommodate a reference cartridge. In this way further housing components, such like a protective cap to cover the cartridge holder and to releasably engage with the cartridge holder can be left completely unaltered.

According to a further embodiment a ratio R of the diameter D2 and the reference diameter D1, namely $$R = \left(\frac{D2}{D1}\right)^2$$

is smaller than 1 but larger than 0.1. In this way dose size increments can be reduced up to a factor of 10 compared to dose increments obtainable with the present drive mechanism when operably engaged with the reference cartridge. So the ratio R just defines the size reduction of the reference volume V1 to the volume V2. The dispensed volumes V1 and V2 differ by the ratio R. Hence, $$V2 = \left(\frac{D2}{D1}\right)^2 * V1.$$

In this way the reduction of the ejected volume and hence the minimum dose increment or the size of discrete dose steps can be easily modified and determined on the basis of the relation of the diameter D2 in comparison to the reference diameter D1.

Generally, the diameters D1 or D2 are substantially constant over almost the entire axial elongation of the tubular-shaped barrel of the respective cartridge. Only near a distal end the barrel may comprise a radially narrowing neck portion adjacent to the distal seal. When referring to the diameters D1 and D2 reference is made to the nominal inner diameter of the proximal end or of an axial middle section of the barrel of the cartridge.

Reducing the diameter of the cartridge and hence of its barrel is also beneficial in that the piston providing a proximal seal for the barrel is also provided with a correspondingly reduced transverse diameter or cross-section. This has the further effect, that a contact surface between the piston and an inside facing portion of the sidewall of the barrel is reduced compared to the reference cartridge. In this way, frictional forces arising from the sealing engagement of the piston and the barrel of the cartridge can be effectively reduced, thereby decreasing mechanical friction for displacing the piston inside the barrel. In effect, static friction as well as dynamic friction between the piston and the barrel can be reduced thereby also decreasing a driving force to be provided by the piston rod in order to expel the medicament from the cartridge.

According to another embodiment the ratio R=n/m, with n and m being integer numbers. When the ratio R is a rational number a further modification of the drive mechanism, especially in terms of indicating the size of a dose actually set can be simplified.

According to another embodiment the ratio R substantially equals one of the following ratios: 1/2, 1/3, 1/4, 1/5, 1/6, 2/3, 2/5, 3/4, 3/5, 4/5 or 5/6. By making use of a ratio R of 1/2 the volume V2 dispensed by a displacement of the piston rod of z1 is just divided by a factor 2 compared to the Volume V1 otherwise dispensed with the reference cartridge. With a ratio R=1/3 the volume V1 is just divided by 3. For the purpose of indicating the size of a dose actually set making use of such rational numbers is of particular benefit. When replacing the reference cartridge by a cartridge with a ratio R=1/2 the size of the dose increments can be divided by a factor 2. If the drive mechanism is originally intended to provide setting of a dose with a step size of 1 IU implementation and use of a diameter reduced cartridge exhibiting a ratio R=1/2 the dosing step size can be reduced to 0.5 IU.

According to another embodiment the drive mechanism comprises a dose indicating member with a dose indicating scale to appear in a window of the housing for indicating a size of a dose actually set, wherein the dose indicating scale is re-sized by the ratio R compared to a reference dose indicating scale that applies or which is applicable with the dose indicating member when the drive mechanism is operably engaged with the reference cartridge. Here the ratio R does not necessarily comprise a rational number but may comprise any positive number between 0.1 and 1.

When replacing the reference cartridge by a diameter reduced cartridge according to the present disclosure it is also of particular benefit also to replace the dose indicating member or at least to replace a dose indicating scale provided thereon. The dose indicating member and almost all further components of the drive mechanism may be manufactured as injection molded plastic components. For replacing a dose indicating scale it may be only necessary to modify the outer appearance of the dose indicating member. It may be sufficient to replace a printed scale on the outer circumference of the dose indicating member. The dose indicating scale may be printed or adhesively attached to the outer circumference of the dose indicating member, e.g. by means of a printed label.

Therefore, replacing the reference dose indicating scale by the dose indicating scale matching to the cartridge actually in use may just require to exchange a printed outer surface of the dose indicating member or to make use of a label provided with the re-sized dose indicating scale, which label is to be adhered to the outer circumference of the dose indicating member. The dose indicating member itself, hence its geometry and its functional implementation in the drive mechanism can remain completely unaltered.

In a further embodiment the dose indicating member comprises a sleeve rotatably supported in the housing. Typically, the dose indicating member is rotatably supported in a body of the housing. The dose indicating member is typically rotatable with regard to a longitudinal axis extending through the symmetry axis of the sleeve. The sleeve of the dose indicating member is further in helical threaded engagement with the housing. The dose indicating scale is hence helically-shaped and is provided on an outer circumference of the sleeve. In other words, the consecutive numbers or symbols representing the size of a dose are provided on the outer circumference of the sleeve in a helical manner so that during dose setting or dose dialing a series of increasing or decreasing numbers shows up in a window of the housing.

In another embodiment the housing comprises at least a body and a cartridge holder connected to the body. The body accommodates the drive mechanism and the cartridge holder accommodates a cartridge. Typically, the cartridge holder is either transparent or comprises at least one window to provide visual inspection of the cartridge and its content. For a mass manufacturing process it may be of particular benefit to provide a cartridge holder preassembly constituted by the cartridge holder with the cartridge arranged therein and to further provide a body preassembly constituted by the body with the drive mechanism assembled therein or thereto. In a final step of assembly, which could be also denoted as 'marriage' the two preassemblies are just connected and mutually interlocked so that the injection device is ready to use or almost ready to use.

The injection device may be configured and designed as a disposable device that is intended to be discarded in its entirety once the content of the cartridge has been expelled. With a disposable device the cartridge holder is typically irreleasably connected to the body which means that a detachment of cartridge holder and body after an initial connection thereof implies a destruction of at least one of cartridge holder or body.

Apart from that it is also conceivable that the injection device is configured as a reusable device, wherein the cartridge holder and the body are releasably connectable. With a reusable device the drive mechanism is further provided with a reset function so as to return the piston rod into an initial axial position during replacement of a cartridge.

According to a further embodiment the cartridge holder comprises a proximal connecting end with an insert section to engage with a receptacle of a distal connecting end of the body. Typically, the cross-section and geometric shapes of the receptacle and of the insert portion mutually match in such a way, that a positive interconnection of receptacle and insert portion can be obtained. Moreover, the insert section may be slidably insertable in axial direction into the receptacle.

The insert section may comprise at least one fastening element to positively engage with a complementary-shaped fastening element of the receptacle. Mutually engageable and complementary-shaped fastening elements of the insert section and the receptacle provide an axial interlock of cartridge holder and body. Typically, the insert section is slidably displaceable inside the receptacle until the mutually corresponding fastening elements of insert section and receptacle engage. Once the fastening elements of insert section and receptacle engage the insert section is axially fixed to the receptacle. Hence, upon mutual engagement of fastening elements of the insert section and the receptacle the cartridge holder is axially fixed to the body and vice versa.

Furthermore and according to another embodiment the cartridge holder comprises an annular flange section on an outside surface axially confining the insert section in the distal direction. A distal portion of the cartridge holder located distally from the flange section further comprises a diameter that is smaller than the diameter of the insert section. Hence, the cartridge holder may comprise a tapered structure towards the distal end so as to fix and to fasten the cartridge therein.

The insert section is axially confined or axially delimited by the radially outwardly extending flange section. The insert section typically comprises or forms a socket portion with an outer diameter that is at least slightly smaller than the outer diameter of the flange section. The receptacle of the body is configured to axially receive the entirety of the insert portion. Hence, the inner diameter of the receptacle matches with the outer diameter of the insert portion so that the insert portion is axially insertable into the receptacle to form the interconnection of cartridge holder and body. The axial extensions of the insert section and of the receptacle mutually match so that the flange section gets in axial abutment with a distally facing axial end face of the sidewall of the body forming the receptacle when the flange section is in a final assembly position inside the receptacle.

Moreover, the sidewall of the receptacle comprises a beveled axial end face that is complementary-shaped to a beveled abutment face of the flange portion. The beveled axial end face of the receptacle's sidewall forms an axial edge or axial end of the receptacle and faces towards the abutment face of the flange portion of the insert section. The beveled axial end face and the beveled abutment face of the receptacle and of the flange portion define an axial abutment of the cartridge holder and the body so as to limit an insert motion of the insert section entering the receptacle. By means of beveled faces the mutual abutment of the sidewall of the receptacle of cartridge holder or body and the correspondingly-shaped flange section of body or cartridge holder inherently provides a tolerance compensation. An axial compression of the beveled surfaces of the flange section and the distal end face of the receptacle leads to a splaying or radial deformation of the sidewalls of the receptacle and/or insert section by way of which a mutual fastening of cartridge holder and body on the basis of positively engaging fastening elements can be facilitated.

By reducing the diameter of the cartridge holder from the proximal end towards the distal end, the proximal connecting end of a diameter reduced cartridge holder can be remain substantially unchanged or unaltered compared to a reference cartridge holder configured to accommodate a reference cartridge. By means of diameter reduced distal section the cartridge holder easily provides a radial support and a radial fixing or clamping of a diameter reduced cartridge.

According to another embodiment the cartridge holder comprises at least three axially extending inner ribs protruding radially inwardly from an inside surface of the cartridge holder. Said inner ribs are further distributed around the inner circumference of the cartridge holder. Furthermore, they are distributed around the inner circumference of the cartridge holder. It is of particular benefit, when the inner ribs are equidistantly or equiangularly distributed or spaced about the inner circumference of the cartridge holder. The at least three inner ribs may extend substantially parallel in axial direction. They may extend across the flange section. Hence, a proximal end of the inner ribs may be located in the proximal portion of the sleeve while a distal end of the inner ribs may be located in the distal portion of the sleeve.

By means of the at least three axially extending inner ribs the flexural strength and mechanical stability of the cartridge holder can be improved. In addition, the inner ribs may provide radial support for the outer circumference of the tubular-shaped cartridge when arranged inside the cartridge holder. In this way the inner ribs effectively act and serve as a radial support structure for the cartridge. Moreover, by means of radially inwardly extending ribs a difference in the outer shape or outer diameter of the proximal portion and the distal portion of the cartridge holder can be effectively reduced. In this way, the difference of the diameter between a standard cartridge and a diameter-reduced cartridge can be compensated by the radial extension of the inner ribs and by the difference in the diameters of the proximal portion and the distal portion of the sleeve.

Typically, there are provided more than just three axially extending inner ribs. For instance, there may be provided four, five, six, seven, eight or even more inner ribs typically equally spaced in circumferential direction to provide a multiple radial support for the cartridge positioned inside the cartridge holder.

Inner ribs or a constantly reducing inner diameter of the cartridge holder in distal direction further serves to axially guide and to align the cartridge inside the cartridge holder. In this way a well-defined axial guiding and a rather precise alignment of the cartridge along the longitudinal axis of the cartridge holder can be obtained. For a smooth distally directed and repeated displacement of the piston rod in the course of subsequent dose delivery procedures it is of particular benefit when the barrel of the cartridge almost exactly co-aligns with the longitudinal extend of the piston rod. In this way a strain of buckling loads to the piston can be effectively reduced and frictional forces between the piston and the side wall of the barrel of the cartridge can be kept substantially constant over the entire displacement path of the piston inside the barrel.

In another aspect the disclosure also relates to a cartridge for an injection device as described above. The cartridge has a tubular-shaped barrel sealed in proximal direction by a piston. The barrel is filled with a liquid medicament to be delivered or to be dispensed by interaction with the injection device. Furthermore, a ratio of an axial length l versus the diameter D2 of the tubular-shaped body is larger than 5, larger than 8 or larger than 10. Hence, the ratio $$\frac{l}{D2}$$

is larger than 5, larger than 8 or larger than 10. Such rather elongated and diameter reduced cartridges are of particular use to provide the intended dosing accuracy or the intended reduction regarding the size of discrete steps of doses to be set and to be dispensed.

According to a further embodiment the filling volume of the cartridge confined by the piston and the sidewall of the barrel is smaller than 2 ml, smaller than 1.8 ml or smaller than 1.6 ml. In particular, the filling volume of the cartridge may be substantially around 1.5 ml. In further embodiments the filling volume of the cartridge may be as small as about 1 ml.

The barrel typically comprises a tubularly-shaped vitreous material, such like glass. A size reduction of the barrel and hence of the cartridge is of particular use to increase the robustness of the cartridge against mechanical impact. A cartridge with a reduced diameter compared to the reference cartridge may inherently comprise an increased structural rigidity and mechanical stability. It may be less susceptible to fracture or cracking in the event of mechanical impact.

In another aspect the disclosure also relates to a method of increasing the dosing accuracy of an injection device. In a first step there is provided an injection device for delivery of a liquid medicament, which injection device has a housing and a drive mechanism. The drive mechanism comprises a piston rod to advance in a distal direction and to butt against a proximally facing surface of a piston of a cartridge. The injection device further has a dose setting member and a dose dispensing member to set and to dispense a dose of the medicament. Said dose may either be a fixed or pre-defined dose or the dose may be user-settable, i.e. the size of the dose may be individually modified by the user himself.

The drive mechanism is configured to advance the piston rod in distal direction by a distance z1 to dispense a reference volume V1 of the medicament when operably engaged with a reference cartridge having a reference diameter D1. In a second step the method of increasing the dosing accuracy comprises arranging a cartridge inside the housing instead of the reference cartridge, wherein the cartridge has a tubular-shaped barrel filled with a liquid medicament and wherein said barrel is sealed in proximal direction by a piston displaceably arranged inside the barrel. The cartridge has a diameter D2 that is smaller than the reference diameter D1. In this way setting and dispensing of a dose of the medicament of a volume V2 is enabled, which volume V2 is smaller than the volume V1 when the piston rod is advanced in distal direction by the distance z1.

The present method implies replacement of a standard cartridge by a cartridge with a reduced diameter while still making use of a substantially unaltered injection device. In particular all mechanically interacting components of the drive mechanism of the injection device can remain unaltered so that the drive mechanism provides an unaltered advancing motion of a piston rod during a dose dispensing procedure. It is only by a well-defined reduction of the diameter of the cartridge that the volume of the medicament dispensed per axial displacement of the piston rod is reduced in a well-defined way.

It may be then only required to slightly modify the geometric size of a pressure piece at a distal end of the piston rod and to eventually modify the geometry of the cartridge holder if the diameter reduction of the cartridge also reflects on the outer diameter thereof. In addition and in order to provide a correct and matching dose size indicator a dose indicating member may have to be equipped with a re-sized dose indicating scale. The dose indicating member itself and its mechanical interaction with other components of the drive mechanism can remain unaltered.

In this way dosing accuracy can be improved and the step size of discreet dose sizes can be reduced without any substantial modifications to the drive mechanism of the injection device.

In a further aspect, the injection device is configured as a manually operable injection device, wherein a force for driving the piston rod in distal direction is entirely provided by a user. The drive mechanism may therefore comprise a dose button or a comparable dose dispensing member that is displaceable in proximal direction with respect to the housing during setting of a dose and which is displaceable in distal direction by the user during dispensing of a dose, thereby transferring a distally directed thrust or a driving torque to the piston rod.

A displacement path of the dose button or dose dispensing member is directly related to a displacement path of the piston rod. The drive mechanism may provide a linear transmission between the axial displacement of the dose button or dose dispensing member and the piston rod. Hence, the displacement path of the dose button or dose dispensing member is typically larger than the displacement path of the piston rod. But the distally directed thrust provided by the piston rod and acting on the piston of the cartridge may be larger than a thrust or force required to displace the dose button or the dose dispensing member in distal direction for inducing or conducting the injection process.

In another aspect, the injection device comprises only cartridge at a time. The injection device and its drive mechanism is configured to operably engage with only one cartridge. The injection device is hence configured as a single-cartridge device. In particular, the cartridge holder of the injection device only receives a single cartridge filled with a medicament. In order to accommodate a cartridge with a reduced diameter in comparison to a reference cartridge the inner diameter of the cartridge holder is also reduced compared to a reference cartridge holder configured to accommodate a reference cartridge.

In a further aspect the drive mechanism comprises a single piston rod to engage with the single cartridge accommodated in the injection device. Hence, the injection device only comprises a single drive mechanism.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a protein, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivatives are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

It will be further apparent to those skilled in the art that various modifications and variations can be made to the present disclosure without departing from the spirit and scope of the disclosure. Further, it is to be noted, that any reference numerals used in the appended claims are not to be construed as limiting the scope of the disclosure.

BRIEF DESCRIPTION OF THE FIGURES

In the following, an embodiment of the disclosure is described in detail by making reference to the drawings, in which.

DETAILED DESCRIPTION

Figure 1:
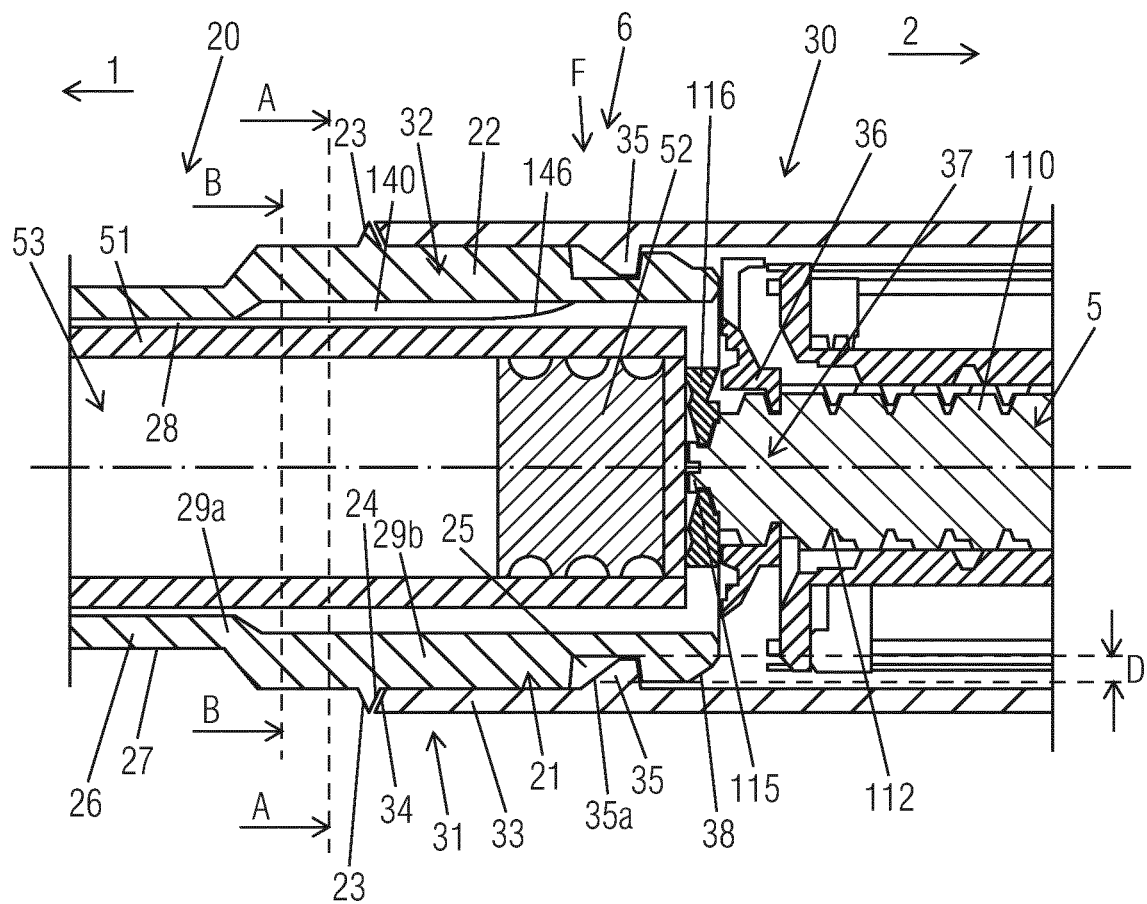
FIG. 1 schematically illustrates an interface of cartridge holder, cartridge, body and drive mechanism of an injection device according to the present disclosure, FIG. 2 schematically shows a reference cartridge in longitudinal cross section.
Figure 7:
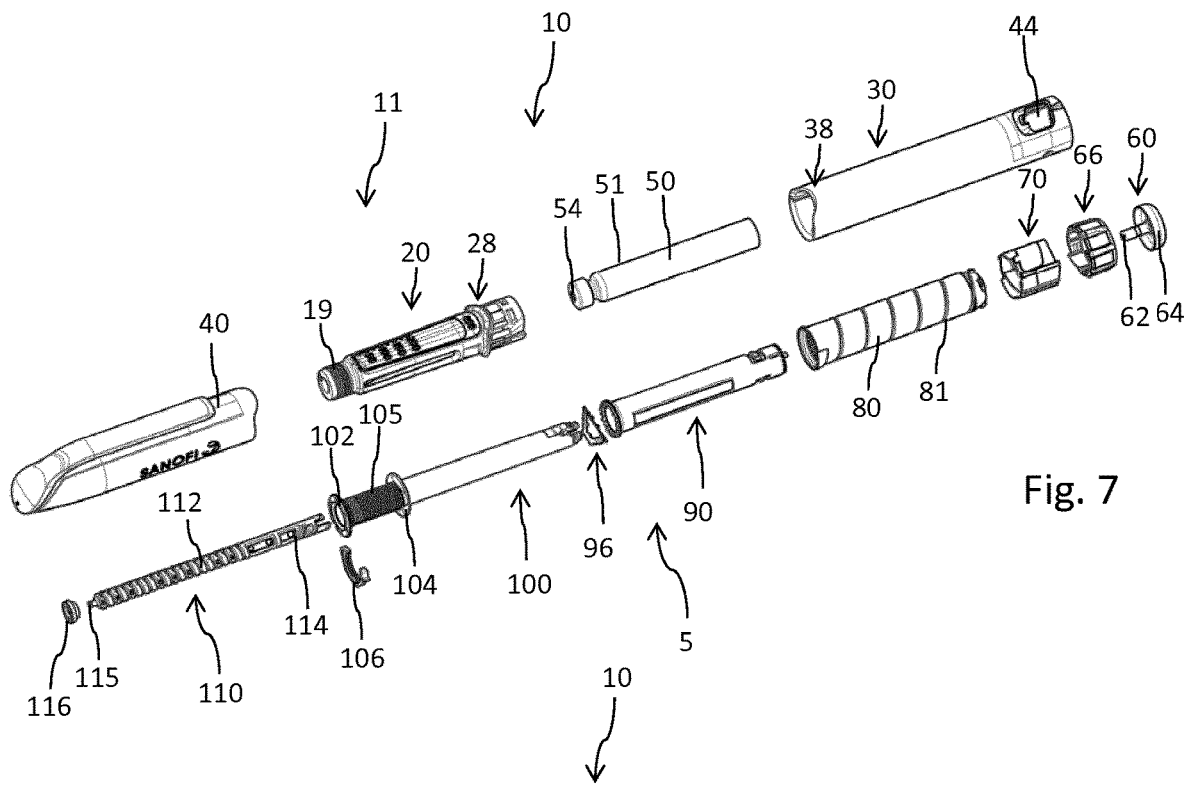
FIG. 7 shows one embodiment of the injection device in an exploded view.
Figure 8:
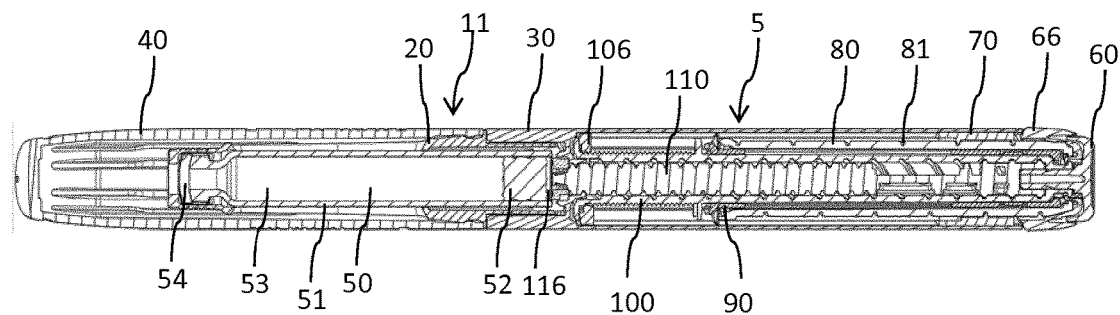
FIG. 8 shows the injection device in a longitudinal cross-section.

The injection device 10 as shown in FIGS. 1, 7 and 8 is configured as a pen-type injector. It comprises an elongated housing 11 extending in a longitudinal or axial direction. Towards a distal direction 1 the injection device 10 comprises a distal housing component denoted as cartridge holder 20. In the opposite longitudinal direction the housing 11 comprises a second housing component denoted as body 30. Both housing components, namely cartridge holder 20 and body 30 are of tubular and elongated shape. The cartridge holder 20 is configured to accommodate a cartridge 50 comprising a tubular-shaped barrel 51 and being filled with a liquid medicament 53. At a distal end the cartridge 50 comprises a pierceable seal 54 typically comprising a pierceable septum of an elastomeric material.

At the opposite proximal end the cartridge 50 is sealed by a piston 52 slidably arranged inside the barrel 51 of the cartridge 50. For dispensing of a dose of the liquid medicament 53 the cartridge holder 20 comprises a threaded socket 19 at its distal end to receive a correspondingly threaded needle assembly with a double-tipped injection needle. A proximal tipped end of the injection needle of the needle assembly, which is presently not illustrated, is configured to pierce the distal seal 54 of the cartridge 50 thereby gaining access to the interior of the cartridge 50. The distal end of the injection needle is then configured to puncture biological tissue to deliver the medicament. For medicament delivery the piston 52 is to be displaced in distal direction 1 under the action of a distally advancing piston rod 110 of a drive mechanism 5 of the injection device 10. The drive mechanism 5 is accommodated and fixed in the body 30 of the injection device 10.

The cartridge holder 20 and the body 30 are to be interconnected by means of a positive connection as it is explicitly shown in FIG. 1. The cartridge holder 20 comprises a proximal connecting end 21 to irreleasably interconnect with a distal connecting end 31 of the body 30. The cartridge holder 20 and the body 30 are interconnectable in an interleaved or nested way. In the presently illustrated embodiment the proximal connecting end 21 of the cartridge holder 20 comprises an insert section 22 axially confined in distal direction 1 by a radially outwardly extending flange section 23. The distal connecting end 31 of the body 30 comprises a receptacle 32 to axially receive the insert section 22 of the cartridge holder 20. The outer diameter of the insert section 22 exactly matches with the inner diameter of the receptacle 32 so that the insert section 22 can be inserted into the receptacle 32 by means of a sliding motion in proximal direction 2 relative to the body 30.

The sidewall 33 of the receptacle 32 comprises a beveled axial end face 34 that forms a distal end of the body 30. The flange section 23 on the outer surface 27 of the cartridge holder 20 comprises a complementary-shaped beveled abutment face 24 featuring a geometric shape that matches with the shape of the beveled axial end face 34 of the sidewall 33. As it is shown in FIG. 1 the beveled abutment face 24 faces in proximal direction 2 whereas the beveled axial end face 34 faces in distal direction 1.

The flange section 23 divides the cartridge holder 20 into a distal portion 29a and a proximal portion 29b. Distal and proximal portions 29a, 29b are separated by the flange section 23 having an annular shape and extending around the entire circumference of the cartridge holder 20. A diameter of the proximal portion 29a is smaller than a diameter of the proximal portion 29b. The proximal portion may coincide with the insert section 22 or may define the insert section 22 of the cartridge holder 20. In this way, the outer shape of the cartridge holder comprises a radially stepped down portion towards the distal end thereby adapted to the reduced diameter of the cartridge 50 located therein.

In order to irreleasably interconnect the cartridge holder 20 and the body 30 in a final assembly or final fastening position F there are provided mutually corresponding fastening elements 35 and 25 on the inside of the receptacle 32 and on the outside of the insert section 22. The body 30 comprises numerous fastening elements 35 radially inwardly extending from the inside of the sidewall 33 of the receptacle 32. The fastening elements are configured as snap features or snap protrusions extending radially inwardly from the sidewall 33 of the receptacle 32.

There are provided several e.g. four fastening elements 35 arranged along the inner circumference of the sidewall 33 of the receptacle 32. The fastening elements 35 are arranged near a flange-like threaded support 36 having a central through opening 37 through which the threaded piston rod 110 extends. The support 36 extends substantially perpendicular to the axial direction and confines the receptacle 32 in proximal direction 2. The support 36 effectively divides the body 30 into a distal interface section formed by the receptacle 32 and a proximal section to accommodate the mechanical components of the drive mechanism 5.

The fastening elements 35 provided on the inside of the sidewall 33 of the receptacle 32 comprise radially inwardly extending protrusions having a beveled section 35a facing in distal direction 1 and extending radially inwardly from the sidewall 33 to the crest of the protruding fastening element 35 to axially abut with a complementary shaped recessed fastening element 25 of the cartridge holder 20. The fastening element 25 comprises a radially extending recessed portion terminated in proximal direction 2 by a radially extending abutment section to axially abut with the fastening element 35. When the cartridge holder 20 and the body 30 are arranged in a final assembly configuration or fastening position F an axial interlock 6 between the fastening elements 25, 35 and hence between the cartridge holder 20 and the body 30 is established.

The proximal end of the cartridge holder 20 comprises a beveled edge 38 at its outer circumference that engages with the beveled section 35a of the protrusion 35 as the insert section 22 is urged in proximal direction 2 into the receptacle 32. The beveled edge 38 is at least located in an angular position on the proximal end of the insert section 22 that matches with an angular position of the respective fastening element 25. The beveled edge facilitates mutual assembly and induces an elastic deformation of both, the sidewall 33 of the receptacle 32 and of the insert section 22. The mutually corresponding fastening elements 25, 35 of cartridge holder 20 and body 30 are subject to tensile stress and to compressive stress during insertion of the insert section 22 into the receptacle 32, respectively.

Since the outer diameter of the insert section 22 matches with the inner diameter of the receptacle 32 an insert and fastening procedure requires elastic deformation of the housing component's cartridge holder 20 and body 30 due to the shape of the mutually corresponding fastening elements 25, 35. The housing components, cartridge holder 20 and body 30 are typically single pieced and are made by way of injection molding of a thermoplastic material.

During mutual assembly, the receptacle 32 and its sidewall 33 experiences a radially outwardly directed load or stress leading to tensile forces in circumferential direction inside the sidewall 33. Correspondingly, the insert section 22 experiences a radially inwardly directed pressure leading to compressive stress in circumferential direction inside the insert section 22. Since thermoplastic materials are more sensitive to tensile than to compressive stress it is of particular benefit, that weakening recessed structures are provided in the insert section of the cartridge holder 20. The radially inwardly extending protrusions of the fastening elements 35 of the body provide a structural reinforcement so that the sidewall 33 in the region of the fastening elements 35 is less susceptible in response to tensile loads that may arise during an assembly procedure.

The recessed fastening elements 25 provided in the insert section 22 of the cartridge holder 20 are configured as blind holes or pocket holes and do not completely intersect the wall structure of the insert section 22. Hence, a radial depth D of the recesses 25 is smaller than the thickness of the sidewall 26 of the insert section 22. Making use blind recesses or pocket holes instead of through openings also enhances and improves the mechanical stability and resistivity against mechanical loads present on the respective fastening element 25 during assembly. As a result a rather rigid, tight and long-term mechanically stable irreleasable connection of cartridge holder 20 and body 30 is provided.

As it is further indicated in FIG. 1 there are also provided inner ribs 140 protruding radially inwardly from an inside surface 28 of the cartridge holder 20. The inner ribs 140 also extend in axial direction. They comprise a beveled proximal end 146. There may be provided numerous, e.g. 5, 6 or even 8 or 10 inner ribs 140 along the inner circumference of the inside surface 28 of the cartridge holder 20. The inner ribs 140 may equidistantly or equiangularly spaced in circumferential or tangential direction so as to provide a radial support for the cartridge 50 arranged inside the sleeve 29.

By way of the radially inwardly extending inner ribs 140 any differences of an outer diameter of the diameter reduced cartridge 50 and an inner diameter of the cartridge holder 20 can be effectively compensated. By means of the beveled proximal ends 146 insertion of the cartridge 50 from a proximal end in distal direction 1 and into the hollow cartridge holder 20 can be facilitated. Also here a mutual radial centering and mutual radial displacement of the cartridge 50 relative to the cartridge holder 20 is obtained as the distal end of the cartridge 50 engages and slides along the beveled proximal ends 146 of the inner ribs 140.

Figure 2:
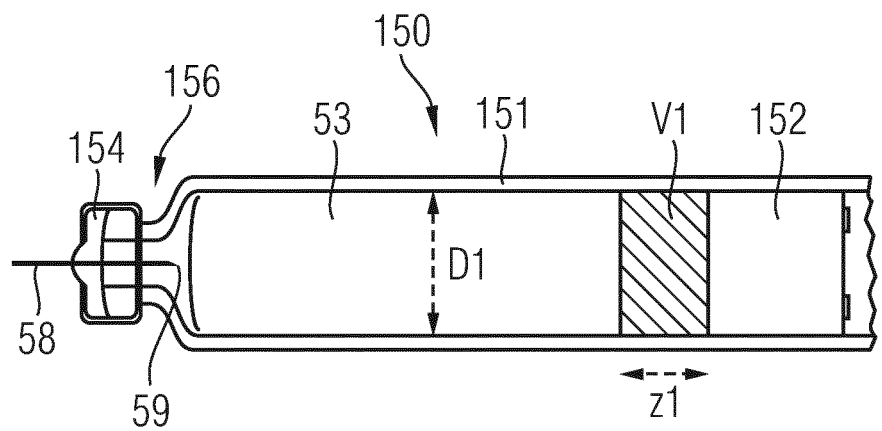
Figure 3:
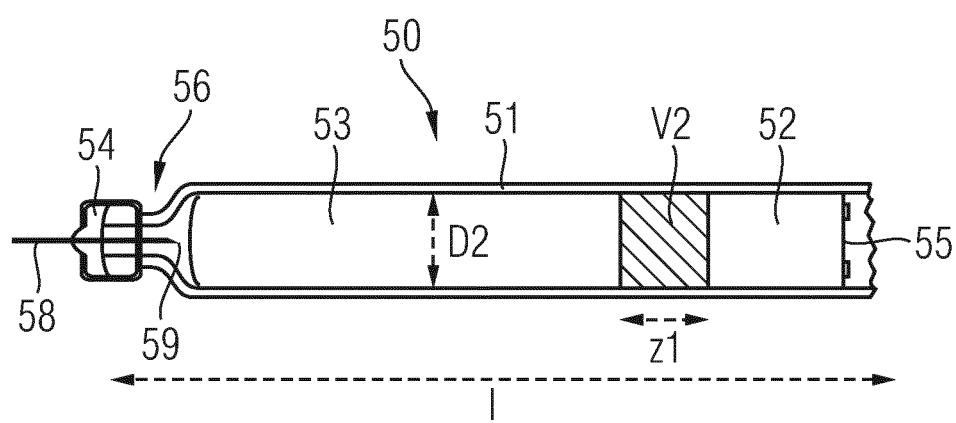
FIG. 3 shows a diameter reduced cartridge compared to the reference cartridge.

In FIGS. 2 and 3 two different cartridges, namely a reference cartridge 150 and a cartridge 50 in accordance with the present disclosure are illustrated, respectively. Both cartridges 50, 150 comprise a tubular-shaped barrel 51, 151 extending in a longitudinal direction that coincides with a cylindrical symmetry axis of the barrels 51, 151. In an axial distal direction 1 the barrels 51, 151 are sealed by a distal seal 54, 154, typically comprising a pierceable septum fixed to a diameter reduced neck portion 56, 156. Typically, the pierceable seal 54, 154 is fixed to a distal end of the barrel 51, 151 by means of a crimped metal cap typically made of aluminum.

As it is further illustrated in FIGS. 2 and 3 the pierceable seal 54, 154 can be axially penetrated by a needle 58. The needle 58 is typically part of a needle assembly comprising a sleeve-shaped needle hub having a fastening structure that is correspondingly-shaped to the threaded socket 19 of the cartridge holder 20. The proximal end of the needle 58 is insertable through a central through opening of the cartridge holder 20 co-aligned with the pierceable sealing 54, 154. In this way the proximal tipped end 59 of the needle 58 can be positioned inside the interior volume of the cartridge 50, 150, thereby providing a fluid channel for the liquid medicament 53 located inside the cartridge 50, 150.

Towards their proximal end the cartridges 50, 150 are sealed by means of a piston 52, 152 typically made of an elastomeric material, such like a natural or synthetic rubber. The piston 52, 152 serves as a proximal seal of the barrel 51, 151. It is displaceable in distal direction 1 under the action of the distally advancing piston rod 110. For injecting of a dose of a predefined size, for instance for injecting of a dose of a reference volume V1 the piston 152 is displaced in distal direction 1 by a distance z1 as shown in FIG. 2. The reference volume V1 is determined by the inner reference diameter D1 of the reference cartridge 150 and the axial displacement distance z1. Hence, the reference volume $$V1 = \left(\frac{D1}{2}\right)^2 \pi * z1.$$

The drive mechanism 5 of the injection device 10 is configured to set and to dispense a reference volume V1 of the medicament 53. Hence, for dispensing of the reference volume V1 the drive mechanism 5 is configured to displace the piston rod 110 by a distance z1.

According to the present disclosure the drive mechanism 5 and hence almost the entire injection device 10 configured and designed for a reference cartridge 150 is now used with a different cartridge 50 as shown in FIG. 3. In comparison to the reference cartridge 150 the cartridge 50 is also of tubular shape but comprises an inner diameter D2 that is smaller than the reference diameter D1. For injecting of a smaller dose compared to the reference volume V1 also here a correspondingly size reduced piston 51 is to be displaced in distal direction by the same distance z1. Due to the reduced diameter D2 compared to the reference diameter D1 the dispensed volume V2 is smaller than the reference volume V1. The ejected volume V2 calculates as $$V2 = \left(\frac{D2}{2}\right)^2 \pi * z1.$$

In this way a size reduced dose of the medicament 53 can be dispensed and injected via the injection needle 58 by making use of one and the same drive mechanism 5. There may be situations and configurations of the drive mechanism 5, where the smallest discrete displacement z1 of the piston rod 110 corresponds or defines a minimum reference volume V1 in the range of 1 IU. By reducing the diameter of the cartridge from D1 to D2 the minimum dispensable size of a dose to be dispensed can be reduced to values smaller than 1 IU. If for instance the area of the inner cross-section of the reference cartridge 150 is divided by 2 with the cartridge 50 the minimum dose size to be dispensed by means of the drive mechanism 5 will be divided by 2. A minimum dose size as well as a discrete step size of selectable doses may then equal e.g. 0.5 IU.

As it is further shown in FIG. 3, the diameter reduced cartridge 50 comprises a ratio of an axial length l over the diameter D2 that is larger than 5, larger than 8 or even larger than 10. Moreover, a total filling volume confined by the piston 52 and the sidewall of the barrel 51 is typically smaller than 2 ml, smaller than 1.8 ml or smaller than 1.6 ml. It may be as small as 1.5 ml or as small as 1 ml. Reducing the diameter of the barrel 51 compared to the reference barrel 151 is further beneficial in terms of a static or dynamic friction between the piston 52 and the inside facing sidewall of the barrel 51. In effect, the total sealing surface on the outer circumference of the piston 52 is reduced compared to the piston 152. In this way, static as well as dynamic friction between the piston 52 and the barrel 51 is typically smaller than dynamic and static friction of the piston 152 and the barrel 151. In effect, dispensing forces that have to be applied to a proximal thrust receiving surface 55 of the piston 52 can be effectively reduced. This is particularly beneficial to increase a handling comfort and ease of use of the injection device.

In FIGS. 7 and 8 one embodiment of an injection device 10 is illustrated comprising a drive mechanism 5 that has been commercially distributed over years and which is described in detail in the following documents: WO 2004/078239 A1, WO 2004/078240 A2 and WO 2004/078241 A1. The injection device 10 is of disposable type. Hence, when the medicament 53 contained in the cartridge 50 has been dispensed or used up the entire device 10 is intended to be discarded. Therefore, the cartridge holder 20 to accommodate the cartridge 50 is irreleasably connectable to the proximal housing component, hence to the body 30. A cap 40 to cover the cartridge holder 20 extending distally from the body 30 is releasably interconnectable with the cartridge holder 20.

The drive mechanism 5 comprises numerous mechanically interacting components. The flange like support 36 of the body 30 comprises a threaded through opening 37 threadedly engaged with a distal thread 112 of the piston rod 110. The distal end of the piston rod 110 comprises a bearing 115 on which a pressure foot 116 is free to rotate with the longitudinal axis of the piston rod 110 as an axis of rotation. The pressure foot 116 is configured to axially abut against the proximally facing thrust receiving surface of the piston 52 of the cartridge 50. During a dispensing action the piston rod 110 rotates relative to the body 30 thereby experiencing a distally directed advancing motion relative to the body 30 and hence relative to the barrel 51 of the cartridge 50. As a consequence, the piston 52 of the cartridge 50 is displaced in distal direction by a well-defined distance due to the threaded engagement of the piston rod 110 with the body 30.

The piston rod 110 is further provided with a second thread 114 at its proximal end. The distal thread 112 and the proximal thread 114 are oppositely handed.

There is further provided a drive sleeve 100 having a hollow interior to receive the piston rod 20. The drive sleeve 100 comprises an inner thread threadedly engaged with the proximal thread 114 of the piston rod 110. Moreover, the drive sleeve 100 comprises an outer threaded section 105 at its distal end. The threaded section is axially confined between a distal flange portion 102 and another flange portion 104 located at a predefined axial distance from the distal flange portion 102. Between the two flange portions 102, 104 there is provided a last dose limiting member 106 in form of a semi-circular nut having an internal thread matching the threaded section 105 of the drive sleeve 100.

The last dose limiting member 106 further comprises a radial recess or protrusion at its outer circumference to engage with a complementary-shaped recess or protrusion at an inside of the sidewall 33 of the body 30. In this way the last dose limiting member 106 is splined to the body 30. A rotation of the drive sleeve 100 in a dose incrementing or clockwise direction during consecutive dose setting procedures leads to an accumulative axial displacement of the last dose limiting member 106 relative to the drive sleeve 100. There is further provided an annular spring 96 that is in axial abutment with a proximally facing surface of the flange portion 104. Moreover, there is provided a tubular-shaped clutch member 90. At a first end the clutch member 90 is provided with a series of circumferentially directed saw teeth. Towards a second opposite end of the clutch member 90 there is located a radially inwardly directed flange.

Furthermore, there is provided a dose dial or dose indicating sleeve 80. The dose indicating sleeve 80 is provided outside of the spring 96 and the clutch member 90 and is located radially inward of the body 30. A helical groove 81 is provided about an outer surface of the dose indicating sleeve 80. The body 30 is provided with a window 44 through which a part of the outer surface of the dose indicating sleeve 80 can be seen. The body 30 is further provided with a helical rib at an inside sidewall portion of an insert piece 70, which helical rib is to be seated in the helical groove 81 of the dose indicating sleeve 80. The tubular shaped insert piece 70 is inserted into the proximal end of the body 30. It is rotationally and axially fixed to the body 30. There are provided first and second stops on the body 30 to limit a dose setting procedure during which the dose indicating sleeve 80 is rotated in a helical motion relative to the body 30.

A dose dial grip 66 is disposed about an outer surface of the proximal end of the dose indicating sleeve 80. An outer diameter of the dose dial 66 typically corresponds to the outer diameter of the body 30. The dose dial 66 is secured to the dose indicating sleeve 80 to prevent relative movement therebetween. The dose dial 66 is provided with a central opening.

Furthermore, a dose button 60 of generally T-shape is provided at a proximal end of the injection device 10. A stem 62 of the dose button 60 extends through the opening in the dose dial 66 through an inner diameter of extensions of the drive sleeve 100 and into a receiving recess at the proximal end of the piston rod 110. The stem 62 is retained for limited axial movement in the drive sleeve 100 and against rotation with respect thereto. A head 64 of the dose button 60 is generally circular. A skirt extends from a periphery of the head 64 and is further adapted to be seated in a proximally accessible annular recess of the dose dial 66.

To dial a dose a user rotates the dose dial 66. With the spring 96 also acting as a clicker and the clutch member 90 engaged, the drive sleeve 100 the spring or clicker 96, the clutch member 90 and the dose indicating sleeve 80 rotate with the dose dial 66. Audible and tactile feedback of the dose being dialed is provided by the spring 96 and by the clutch member 90. Torque is transmitted through saw teeth between the spring 96 and the clutch member 90. The helical groove 81 on the dose indicating sleeve 80 and a helical groove in the drive sleeve 100 have the same lead. This allows the dose indicating sleeve 80 to extend from the body 30 and the drive sleeve 100 to climb the piston rod 110 at the same rate. At a limit of travel a radial stop on the dose indicating sleeve 80 engages either with a first stop or a second stop provided on the body 30 to prevent further movement. Rotation of the piston rod 110 is prevented due to the opposing directions of the overall and driven threads on the piston rod 110.

The last dose limiting member 106 keyed to the body is advanced along the threaded section 105 by the rotation of the drive sleeve 100. When a final dose dispensed position is reached, a radial stop formed on a surface of the last dose limiting member 106 abuts a radial stop on the flange portion 104 of the drive sleeve 100, preventing both, the last dose limiting member 106 and the drive sleeve 100 from rotating further.

Should a user inadvertently dial beyond the desired dosage, the pen-injector 10 allows the dosage to be dialed down without dispense of the medicament from the cartridge 50. For this the dose dial 66 is simply counter-rotated. This causes the system to act in reverse. A flexible arm of the spring or clicker 96 then acts as a ratchet preventing the spring 96 from rotating. The torque transmitted through the clutch member 90 causes the saw teeth to ride over one another to create the clicks corresponding to dialed dose reduction. Typically, the saw teeth are so disposed that a circumferential extent of each saw tooth corresponds to a unit dose.

When the desired dose has been dialed the user may simply dispense the set dose by depressing the dose button 60. This displaces the clutch member 90 axially with respect to the dose indicating sleeve 80 causing dog teeth thereof to disengage. However, the clutch member 90 remains keyed in rotation to the drive sleeve 100. The dose indicating sleeve 80 and the dose dial 66 are now free to rotate in accordance with the helical groove 81.

The axial movement deforms the flexible arm of the spring 96 to ensure the saw teeth cannot be overhauled during dispense. This prevents the drive sleeve 100 from rotating with respect to the body 30 though it is still free to move axially with respect thereto. The deformation is subsequently used to urge the spring 96 and the clutch member 90 back along the drive sleeve 100 to restore the connection between the clutch member 90 and the dose indicating sleeve 80 when the distally directed dispensing pressure is removed from the dose button 60.

The longitudinal axial movement of the drive sleeve 100 causes the piston rod 110 to rotate through the through opening 37 of the support 36 of the body, thereby to advance the piston 52 in the cartridge 50. Once the dialed dose has been dispensed, the dose indicating sleeve 80 is prevented from further rotation by contact of a plurality of members extending from the dose dial 66 with a corresponding plurality of stops. A zero dose position is finally determined by the abutment of one of axially extending edges of members of the dose indicating sleeve 80 with a corresponding stop of the body 30.

The drive mechanism 5 as described above is only exemplary for one of a plurality of differently configured drive mechanisms that are generally implementable in a disposable pen-injector. Hence, one concept of the present disclosure, namely to modify, in particular, to reduce the diameter of a cartridge by means of a respective cartridge replacement is generally implementable with a large variety and with almost all types of injection devices comprising a cartridge filled with a medicament and being sealed by a piston for expelling of a dose of the medicament.

Figure 4:
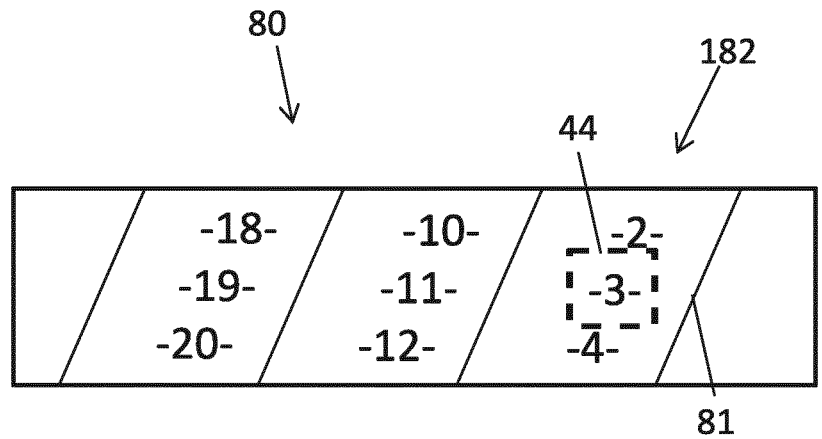
FIG. 4 shows a dose indicating sleeve with a reference dose indicating scale.

When replacing a standard or reference cartridge 150 by a diameter reduced cartridge 50 all mechanically interacting components of the drive mechanism 5 may remain unchanged or unmodified. This is also valid for the dimensions and the geometry of the dose indicating member 80, presently configured as a dose indicating sleeve 88. In FIG. 4, one example of a dose indicating sleeve 88 provided with a reference dose indicating scale 182 is shown in comparison to the location of the dose indicating window 44 of the body 30. As can be seen from FIG. 4, the dose indicating sleeve 88 comprises a helical structure on its outer circumference having the shape and form of a helical groove 81. Accordingly, the outer circumference of the tubular-shaped dose indicating sleeve 88 is provided with a reference dose indicating scale 182 with consecutive integer numbers 1, 2, 3, 4 and so on representing integer IU.

Figure 5:
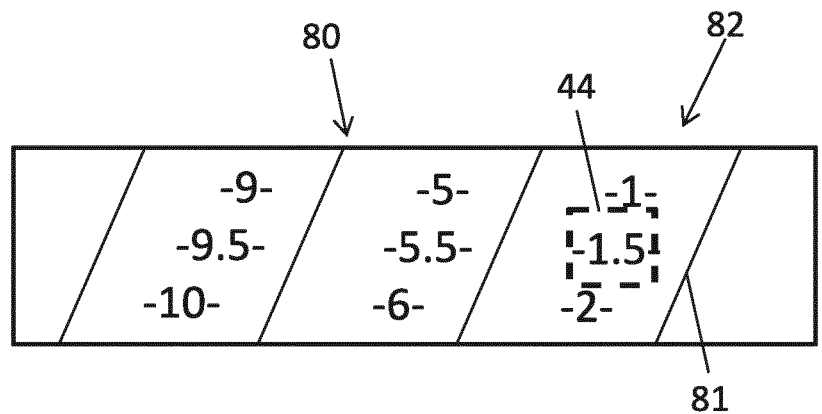
FIG. 5 shows the dose indicating sleeve with a re-sized dose indicating scale.
Figure 6:
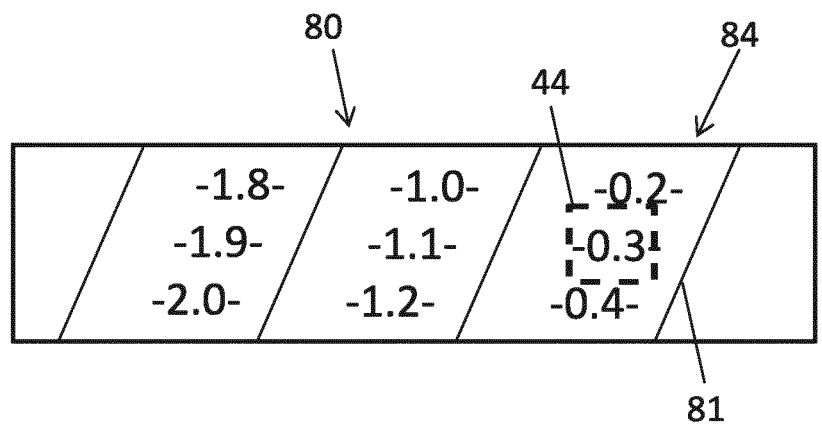
FIG. 6 shows a further embodiment of a dose indicating sleeve with still another re-sized dose indicating scale.

When making use of a diameter reduced cartridge 50 the reference dose indicating scale 182 on the outer circumference of the dose indicating sleeve 88 has to be replaced by a resized dose indicating scale 82 or 84 as shown for instance in FIGS. 5 and 6, respectively. The dose indicating scale 82 as shown in FIG. 5 is applicable when the inner cross-section of the cartridge 50 is reduced by a factor 2 compared to the inner cross-section of the reference cartridge 150. Consequently, the numbers of the reference dose indicating scale are divided by the factor 2. The dose indicating scale 82 of the dose indicating sleeve 88 is configured to show a sequence of numbers such like 0.1, 1, 1.5, 2, and so on.

In FIG. 6 another resized dose indicating scale 84 is presented that is applicable when the inner cross-section of the reference cartridge 150 is divided by a factor 10. Such a resized dose indicating scale 84 on the outer circumference of a geometrically unmodified dose indicating sleeve 88 is provided a sequence of consecutive numbers such as 0.1, 0.2, 0.3, 0.4 and so on.

LIST OF REFERENCE NUMBERS

1 distal direction
2 proximal direction
5 drive mechanism
6 axial interlock
10 injection device
11 housing
19 threaded socket
20 cartridge holder
21 proximal connecting end
22 insert section
23 flange section
24 abutment face
fastening element
26 sidewall
27 outside surface
28 inside surface
29a distal portion
29b proximal portion
30 body
31 distal connecting end
32 receptacle
33 sidewall
34 end face
35 fastening element
35a beveled section
36 support
37 through opening
38 beveled edge
40 cap
44 window
50 cartridge
51 barrel
52 piston
53 medicament
54 distal seal
55 surface
56 neck portion
58 needle
59 proximal end
60 dose button
62 stem
64 head
66 dose dial
70 insert piece
80 dose indicating member
81 helical groove
82 dose indicating scale
84 dose indicating scale
88 dose indicating sleeve
90 clutch member
96 spring
100 drive sleeve
102 distal flange portion
104 flange portion
105 threaded section
106 last dose limiting member
110 piston rod
112 distal thread
114 proximal thread
115 bearing
116 pressure foot
150 cartridge
151 barrel
152 piston
154 distal seal
156 neck portion
182 reference dose indicating scale

The invention claimed is:

1. An injection device for delivery of a liquid medicament, the injection device comprising:
a housing;
a cartridge comprising a barrel, the barrel having a tubular shape, being filled with the liquid medicament, and being sealed at a proximal end by a piston displaceably arranged in the barrel; and
a drive mechanism comprising a piston rod configured to advance in a distal direction against a proximally facing surface of the piston of the cartridge,
wherein the drive mechanism is configured to advance the piston rod in the distal direction by a distance z1 to dispense a reference volume V1 of the liquid medicament when the drive mechanism is operably engaged with a reference cartridge having a reference diameter $D1$, wherein the cartridge has a diameter $D2$ that is less than the reference diameter $D1$ to dispense a volume $V2$ of the liquid medicament that is less than the reference volume $V1$ when the piston rod advances in the distal direction by the distance $z1$, wherein a ratio $R=$(the volume $V2$)/(the reference volume $V1$)$=$[(the diameter $D2$)/(the reference diameter $D1$)]$^2$, wherein the ratio $R$ is less than 1 and greater than 0.1, wherein the drive mechanism further comprises a dose indicating member with a dose indicating scale arranged to appear in a window of the housing for indicating a size of a set dose, and wherein the dose indicating scale is configured to be replaced by a reference dose indicating scale that is applicable with the dose indicating member when the drive mechanism is operably engaged with the reference cartridge such that the dose indicating scale is resized by the ratio $R$ as compared to the reference dose indicating scale.

2. The injection device according to claim 1, wherein the ratio R is further equal to an integer number n divided by an integer number m.

3. The injection device according to claim 1, wherein the dose indicating member comprises a sleeve rotatably supported in the housing and being in helical threaded engagement with the housing, and wherein the dose indicating scale is helically shaped and is provided on an outer circumference of the sleeve.

4. The injection device according to claim 1, wherein the ratio R is between 1/6 and 5/6.

5. The injection device according to claim 4, wherein the ratio R is between 1/6 and 1/2.

6. The injection device according to claim 4, wherein the ratio R is between 1/2 and 5/6.

7. The injection device according to claim 4, wherein the ratio R is between 1/3 and 2/3.

8. The injection device according to claim 1, wherein the housing comprises:
    a body accommodating the drive mechanism, and
    a cartridge holder connected to the body and accommodating the cartridge.

9. The injection device according to claim 8, wherein the cartridge holder comprises at least three axially extending inner ribs protruding radially inwardly from an inside surface of the cartridge holder and being distributed around an inner circumference of the cartridge holder.

10. The injection device according to claim 8, wherein the cartridge holder comprises a proximal connecting end with an insert section configured to engage with a receptacle of a distal connecting end of the body.

11. The injection device according to claim 10, wherein the cartridge holder comprises an annular flange section on an outside surface confining the insert section in the distal direction, and wherein a distal portion of the cartridge holder located distally from the flange section comprises a diameter that is less than a diameter of the insert section.

* * * * *